United States Patent [19]
Koshino

[11] Patent Number: 6,102,952
[45] Date of Patent: *Aug. 15, 2000

[54] MEDICAL SUBSTITUTING ELEMENT FOR HARD TISSUES AND ARTIFICIAL JOINT

[76] Inventor: Tomihisa Koshino, 28-12, Maruyamadai 2-chome, Konan-ku, Yokohama-shi, Kanagawa-ken, Japan

[ * ] Notice: This patent is subject to a terminal disclaimer.

[21] Appl. No.: 09/127,604

[22] Filed: Jul. 31, 1998

Related U.S. Application Data

[63] Continuation of application No. 08/625,899, Apr. 1, 1996, Pat. No. 5,879,389.

[30] Foreign Application Priority Data

Apr. 7, 1995 [JP] Japan ................................ 7-082687

[51] Int. Cl.⁷ ...................................................... A61F 2/00
[52] U.S. Cl. .................................................................. 623/18
[58] Field of Search .......................................... 623/18–20

[56] References Cited

U.S. PATENT DOCUMENTS

| | | |
|---|---|---|
| 1,179,136 | 4/1916 | Ollis . |
| 1,395,286 | 11/1921 | Mennie . |
| 1,410,387 | 3/1922 | Dodds . |
| 2,107,604 | 2/1938 | Friday . |
| 2,288,123 | 6/1942 | Coy . |
| 4,640,524 | 2/1987 | Sedlmair . |
| 4,668,469 | 5/1987 | Widener . |
| 4,673,407 | 6/1987 | Martin . |
| 4,905,546 | 3/1990 | Kätzscher et al. . |
| 5,019,103 | 5/1991 | Van Zile et al. . |
| 5,534,027 | 7/1996 | Hodorek . |
| 5,609,641 | 3/1997 | Johnson et al. . |

*Primary Examiner*—Michael J. Milano
*Attorney, Agent, or Firm*—Nixon & Vanderhye P.C.

[57] ABSTRACT

The invention solves a problem associated with a conventional medical substituting element for hard tissues that loosening is likely to occur after the substituting element is mounted on hard tissues, by providing the medical substituting element for hard tissues with: one or a plurality of through hole units into which fixation screws are inserted; a screw stopper for stopping the fixation screw inserted into the through hole unit at the position where the head of the fixation screw becomes lower than the upper end of the through hole unit; and a slip-off prevention member engaging unit formed in the inner wall of the through hole unit at the position higher than the screw stopper, wherein after the fixation screw inserted into the through hole unit is threaded into the hard tissues, a slip-off prevention member engages with the slip-prevention member engaging unit to ensure a slip-off prevention of the fixation screw.

14 Claims, 8 Drawing Sheets

MEDICAL SUBSTITUTING ELEMENT FOR HARD TISSUES AND ARTIFICIAL JOINT

This is a continuation of application Ser. No. 08/625,899, filed Apr. 1, 1996, now U.S. Pat. No. 5,879,389, issued Mar. 9, 1999.

TECHNICAL FIELD

The present invention relates to a medical substituting element for hard body tissues and an artificial joint which are used as a substitute for part or the whole of the function of damaged hard tissues such as a bone, ligament, and tendon, during its treating period or semipermanently, and more particularly to a medical substituting element for hard tissues of the type that the element can be mounted on the hard tissues with fixation screws, and to an artificial joint which is partially constituted by the element.

BACKGROUND ART

Various medical substituting elements for hard tissues have been developed which are used as a substitute for part or the whole of the function of hard tissues such as a bone, ligament, and tendon impaired by an accident or the diseases such as rheumatism or osteoarthritis, during its treatment period or semipermanently.

For example, for medical treatment of a fracture, a fixation metal jig (bone fixation plate) is often used as the medical substituting element for hard tissues. This fixation metal jig is made of medical metal materials such as stainless steel, cobalt-chrome alloy, titanium, and titanium alloy. After a fracture is reduced and while the fracture is cured, the fixation metal jig is kept attached to a fracture with fixation screws, the jig traversing the broken position of the bone.

For medical treatment of a damaged ligament or a tendon, reconstruction and reinforcement are carried out using the tendon or fascia, or often using an artificial ligament or tendon. For the reconstruction and reinforcement by an artificial ligament or tendon, one or both ends of the artificial ligament or tendon are mounted with a reinforcing member such as a device with a boss which is fixed to the bone with fixation screws to thus fix the artificial ligament or tendon.

For medical treatments of a impaired joint, an artificial joint is often used as the medical substituting element for hard tissues. Artificial joints of various structures developed for specific applications include a hinge type, a hemi-hinge type, a rotating hinge type, a surface replacement type, a constraint surface replacement type, a stabilizer type, a meniscus bearing type, an unicompartmental replacement type, a tibia plateau type, an non-constraint type, and a hemi-constraint type.

Artificial joints are classified into two types, one having a constituent mounted on a bone with fixation screws and the other not having a constituent mounted on a bone with fixation screws. For example, an artificial knee joint of a conventional unicompartmental replacement type (a kind of surface replacement types) is of the type not having a constituent mounted on a bone with fixation screws. For example, an artificial knee joint of such an unicompartmental replacement type has a structure such as shown in FIG. 8.

FIG. 8(a) is a front view illustrating an artificial knee joint 30 of an unicompartmental replacement type when in use, and FIG. 8(b) is a side view of the artificial knee joint 30 when in use. The artificial knee joint 30 (for right knee) shown in FIGS. 8(a) and 8(b) has a tibial component 33 and a femoral component 34, the tibial component 30 being constituted by a tibial tray 31 and a tibial bearing insert 32 fixedly pre-mounted on the upper surface (the surface face to the side of the femoral side when in use) of the tibial tray 31.

The tibial tray 31 has a plate unit 31a, and one long stem 31b and one short stem 31c formed on the bottom surface of the plate unit and slightly slanted, respectively made of medical metal materials including stainless steel such as SUS-316 type, cobalt-chrome-nickel alloy (COP), cobalt-chrome alloy (Vitallium), titanium, titanium alloy, and the like, medical ceramics materials including alumina, zirconia, hydroxyapatite, glass ceramics, and the like, or other medical materials.

The tibial bearing insert 32 is made of high density polyethylene (HDP), ultra-macromolecular polyethylene, or the like, and has a predetermined curve surface at its joint surface (the surface in contact with the femoral component 34 when in use). As described earlier, the tibial bearing insert 32 is fixedly pre-mounted on the upper surface of the tibial tray 31 and functions as a slide member for the femoral component 34.

The femoral component 34 has a plate unit 34a curved in a predetermined shape and two stems 34b formed on this plate unit 34a, respectively made of material including the above-described medical metal, ceramics, and other materials.

As described earlier, the artificial knee joint 30 is a unicompartmental replacement type artificial knee joint, and as shown in FIG. 9 substitutes part of the function of the knee joint. In mounting the artificial knee joint 30, the tibial component 33 is mounted on the proximal end of the tibia 40 at a predetermined position, and the femoral component 34 is mounted on the distal end of the femur 41 at a predetermined position.

In mounting the tibial component 33 on the tibia 40, for example, a predetermined area of the proximal end of the tibia 40 is ground to form a flat surface, two holes for striking the two stems 31b and 31c of the tibial component 33 thereinto are formed in the flat surface area, thereafter the end of the longer stem 31b is first inserted into its hole, the tibial component 33 is rotated using the longer stem 31b as a fulcrum, and when the shorter stem 31c reaches its hole, the stems 31b and 31c are further struck into the holes. In mounting the tibial component 33, bone cement is also used if necessary.

On the other hand, in mounting the femoral component 34 on the femur 41, for example, after a guide hole, into which the stem 34b of the femoral component 34 is struck, is formed in the distal end of the femur 41 at a predetermined position, the distal end of the femur 41 is ground at a predetermined area and thereafter, the stem 34b is struck into the femur 41 along the guide hole. In mounting the femoral component 34, bone cement is also used generally. Reference numeral 42 shown in FIG. 9 represents a fibula.

Although a conventional medical substituting element for hard tissues of a type which is mounted on the hard tissues with fixation screws, is fixed to the hard tissues with fixation screws, a small degree of freedom is practically provided between the substituting element and fixation screws even after the mounting. The reason is that in order not to transmit an impact force applied to the hard tissues directly to the medical substituting element for hard tissues via the fixation screws, the fixation screws are given a capability of changing the direction of the impact force to provide a cushioning function. The other reason is that reverse rotation of the fixation screws is prevented in order for the medical substituting element for hard tissues not to be moved back outside. To this end, in a conventional medical substituting element for hard tissues, a through hole unit into which a fixation screw is entered is not formed with female threads, but only an engaging unit is provided which engages with the head of a fixation screw when it is threaded into the hard tissues to a certain degree, and restricts the further threading.

However, even if a medical substituting element for hard tissues is mounted with a degree of freedom between the element and fixation screws, vibrations applied to the hard tissues mounted with the medical substituting element transmit directly to the fixation screws, so that the fixation screws are spontaneously rotated and moved back outside, causing loosening of the medical substituting element, one of combined diseases.

Such loosening of a medical substituting element for hard tissues often occurs even for the type having a constituent mounted on a bone with stems struck into the bone, such as the conventional artificial knee joint of the unicompartmental replacement type shown in FIGS. 8 and 9. This occurrence frequency is conspicuous particularly for a constituent unable to use a long fixation stem, such as a tibial component.

DISCLOSURE OF THE INVENTION

It is a first object of the present invention to provide a medical substituting element for hard tissues to prevent loosening thereof after it is mounted on hard tissues.

It is a second object of the present invention to provide an artificial joint to prevent loosening thereof after it is mounted on hard tissues.

A medical substituting element for hard tissues of the present invention achieving the first object comprises: one or a plurality of through hole units into which fixation screws are inserted; a screw stopper for stopping the fixation screw inserted into the through hole unit at the position where the head of the fixation screw becomes lower than the upper end of the through hole unit; and a slip-off prevention member engaging unit formed in the inner wall of the through hole unit at the position higher than the screw stopper, wherein after the fixation screw inserted into the through hole unit is threaded into hard tissues, a slip-off prevention unit engages with the slip-prevention member engaging unit to ensure a slip-off prevention of the fixation screw.

An artificial joint of this invention achieving the second object and having a first constituent member mounted on a ground surface formed on one bone constituting a joint and a second constituent member mounted on a ground surface formed on the other bone constituting the joint, the first and second constituent members abutting against each other directly or via a slide member, or being coupled together by a member with an open/close mechanism, wherein the first or second constituent member comprises: one or a plurality of through hole units into which fixation screws are inserted; a screw stopper for stopping the fixation screw inserted into the through hole unit at the position where the head of the fixation screw becomes lower than the upper end of the through hole unit; and a slip-off prevention member engaging unit formed in the inner wall of the through hole unit at the position higher than the screw stopper, wherein after the fixation screw inserted into the through hole unit is threaded into hard tissues, a slip-off prevention member engages with the slip-prevention member engaging unit to ensure a slip-off prevention of the fixation screw.

As described above, with a medical substituting element for hard tissues and an artificial joint of this invention, the slip-off prevention member can prevent the fixation screw from spontaneously rotating and moving back outside after the element is mounted on hard tissues. Therefore, loosening of the medical substituting element for hard tissues is hard to occur, which might otherwise be caused by spontaneous rotation of the fixation screw after the element is mounted on the hard tissues. It is therefore easy to alleviate combined disease by using the medical substituting element for hard tissues and the artificial joint of this invention.

MOST PREFERRED EMBODIMENTS PRACTICING THE INVENTION

The invention will be described in detail.

First, a medical substituting element for hard tissues of this invention will be described. This medical substituting element for hard tissues is a medical substituting element fixed to hard tissues by fixation screws. The invention relating to a medical substituting element for hard tissues is applicable to a fixation metal jig (bone fixation plate) for surgical treatment of a fracture, a an augmentation material (a device with a boss) for an artificial ligament or an artificial tendon, an artificial bone which is fixed to a bone with screws, a tibial tray, a tibial component and a femoral component of an artificial knee joint, an acetabular component of an artificial hip joint, a tibial component and a talar side component of an artificial ankle joint, an acetabular component of an artificial shoulder, a humeral component and an ulnar component of an artificial elbow, an artificial bone head, and the like.

Figure 8A:
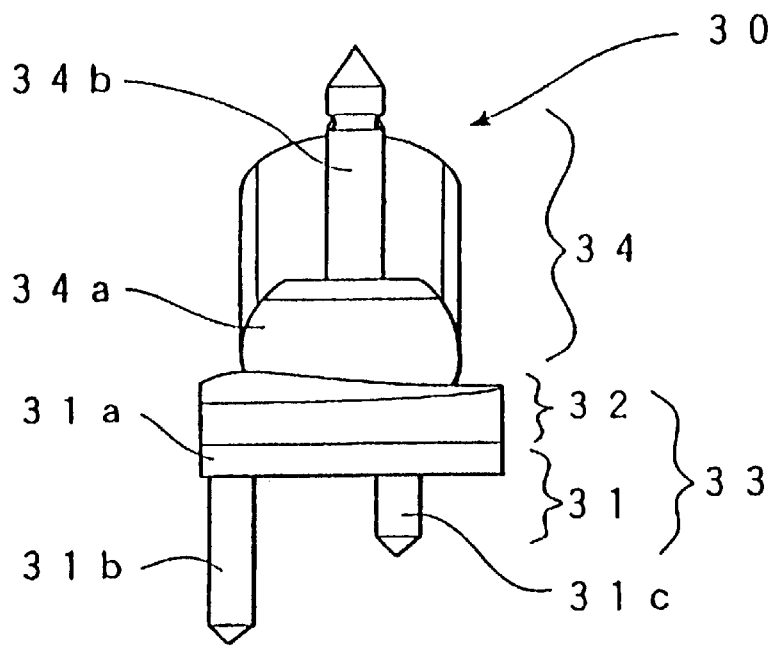
FIG. 8(a) is a front view showing an example of a conventional artificial knee joint of a unicompartmental replacement type.
Figure 8B:
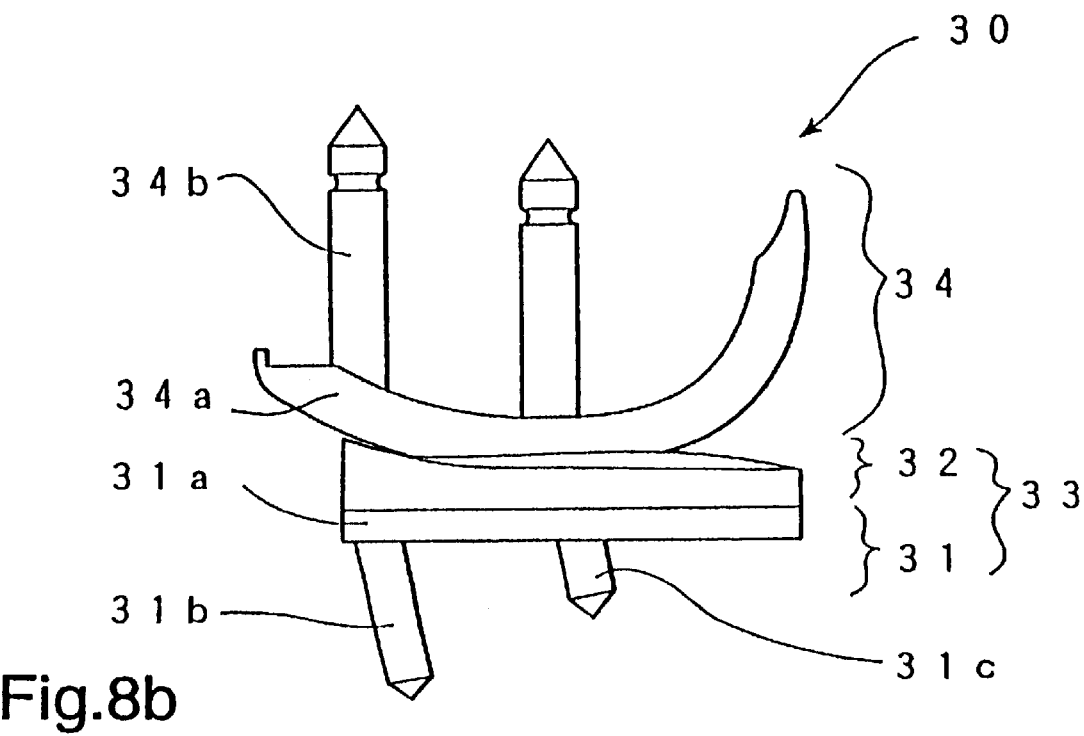
FIG. 8(b) is a side view of the artificial knee joint of the unicompartmental replacement type shown in FIG. 8(a).
Figure 9:
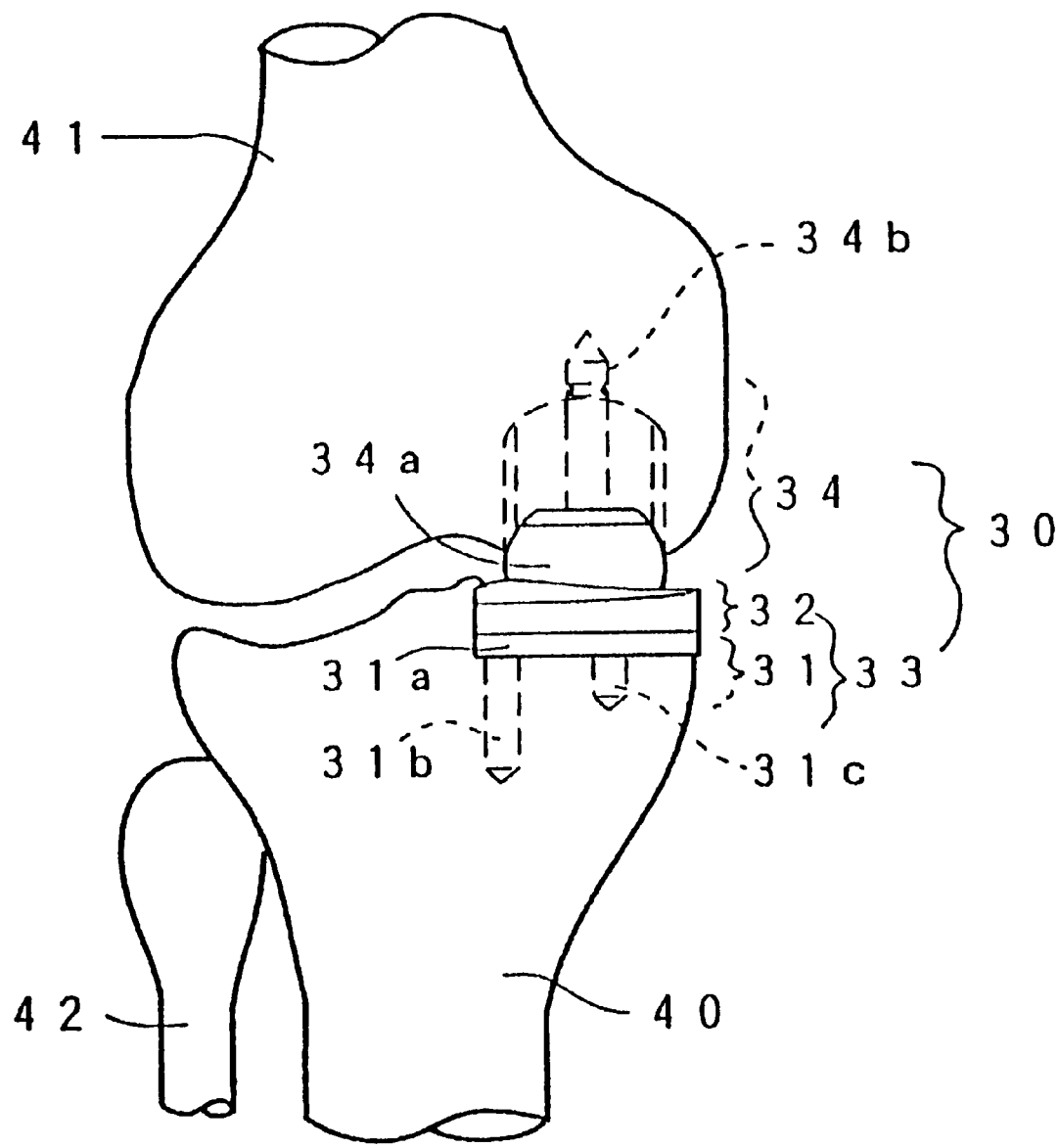
FIG. 9 is a front view illustrating a use state of the artificial knee joint of the unicompartmental replacement type shown in FIG. 8.

The overall shape of the medical substituting element for hard tissues of this invention is not limited in particular, but may be selected as desired in accordance with each application or the like of a subject medical substituting element for hard tissues. For example, if a subject medical substituting element for hard tissues is a fixation metal jig (bone fixation plate) for surgical treatment of a fracture, the overall structure may be rectangular and L-shaped in a side view similar to a conventional shape. If a subject medical substituting element for hard tissues is a an augmentation material (a device with a boss) which is mounted on the end of an artificial ligament of an artificial tendon, this shape may also be a conventional shape. If a subject medical substituting element for hard tissues is a constituent of an artificial joint, a conventional overall shape may be used although it depends on the type of a joint to be replaced by the artificial joint and on which of the two bones constituting the joint the constituent is mounted. For example, if a subject medical substituting element for hard tissues is a tibial component of an artificial knee joint, its plane view may be circular, oval, of horse saddle, or of other shapes. If a subject medical substituting element for hard tissues is a acetabular or glenoidal component of an artificial hip joint or an artificial shoulder, the plane view May be circular, oval, or of other shapes. If a subject medical substituting element for hard tissues is a tibial component or a talus component of an artificial ankle joint, the plane view may be rounded rectangular, rounded trapezoidal, or of other shapes. If a subject medical substituting element for hard tissues is a humeral component or an ulnar component of an artificial elbow, the plane view may be rectangular, ellipsoidal, circular, or of other shapes. If a subject medical substituting element for hard tissues is a constituent of an artificial joint as described above, a slide member (e.g., corresponding to the tibial bearing insert 32 of the tibial component 30 shown in FIG. 8) made of polyethylene, ceramics, or the like may be fixedly pre-mounted or it may be mounted detachably. In the latter case, an engagement unit for detachably mounting the slide member is formed if necessary at a predetermined area of the medical substituting element for hard tissues.

The material of the medical substituting element for hard tissues can be selected as desired from medical inorganic solid materials in accordance with its application. Particular examples of the medical inorganic solid materials are medical metal materials including stainless steel such as SUS-316 type, cobalt-chrome-nickel alloy (COP), cobalt-chrome alloy (Vitallium), titanium, titanium alloy, and the like, medical ceramics materials including alumina, zirconia, hydroxyapatite, glass ceramics, sapphire, and the like, bone materials including glass, glass fibers, kiel bones, and the like, macromolecular materials such as synthetic resin and the like including polypropylene, polyethylene, and the like, poly-lactic-acid materials, and other medical materials.

As stated earlier, the medical substituting element for hard tissues of this invention has one or a plurality of through hole units into which fixation screws are inserted. The number of through hole units can be selected as desired depending on the application or the like of the medical substituting element for hard tissues. The thickness of a member at which the through hole unit is formed is optional so long as a slip-off prevention member engaging unit to be described later can be formed in the inner wall of the through hole unit. If the medical substituting element for hard tissues is a plate unit, a projection is formed on the bottom surface of the plate unit at the position where the through hole unit is formed, and the through hole unit is formed passing through the projection, so that a space for forming the slip-off prevention engaging unit to be described later can be easily reserved.

Into the through hole unit, a fixation screw is inserted for mounting the medical substituting element to hard tissues. Although a female thread portion meshing with the fixation screw is generally unnecessary to be formed in the through hole unit, it may be formed if necessary. A screw stopper is formed in the through hole unit, and stops the inserted fixation screw at the position where the head of the fixation screw becomes lower than the upper end of the through hole unit. As the fixation screw inserted into the through hole unit continues to be threaded into the hard tissues, the screw stopper and the head of the fixation screw abut against each other to restrict the threading of the fixation screw. In mounting the medical substituting element for hard tissues, the screw stopper and the head of the fixation screw may be abutted together or may leave a desired amount of gap therebetween.

Formed in the inner wall of the through hole unit at the position higher than the screw stopper is the slip-off prevention member engaging unit which is the most significant feature of the medical substituting element for hard tissues of this invention. This slip-off prevention member engaging unit engages with a slip-off prevention member for preventing an spontaneous rotation and slip-off of the fixation screw once threaded into the hard tissues. The configuration of the slip-off prevention member engaging unit is selected as desired in accordance with the configuration of a member used as the slip-off prevention member.

Particular examples of the slip-off prevention member to be enumerated are a screw (hereinafter called a stopper screw) having a threading rotation direction opposite to the fixation screw, a ring stopper, a caulking projection formed on the head of the fixation screw, and the like.

If the stopper screw is used as the slip-off prevention member, a female tread portion meshing with the stopper screw is used as the slip-off prevention engaging unit. For example, if the fixation screw is a right-handed screw, a left-handed screw is used as the slip-off prevention screw. Therefore, the female thread portion meshing with the left-handed screw (slip-off prevention screw) is used as the slip-off prevention member engaging unit. If the fixation screw is a left-handed screw, a right-handed screw is used as the slip-off prevention screw. Therefore, the female thread portion meshing with the right-handed screws (slip-off prevention screw) is used as the slip-off prevention member engaging unit.

Whether a right- or left-handed screw is used as the fixation screw is decided as desired, and in correspondence with this decision, whether a left- or right-handed screw of the female screw portion is formed as the slip-off prevention member engaging unit is decided selectively. The slip-off prevention screw may be a screw whose head extends out of the upper edge of the through hole unit or may be a screw whose head is substantially flush with, or lower than, the upper edge of the through hole unit. If a subject medical substituting element for hard tissues is a constituent of an artificial joint, it is particularly preferable that the slip-off prevention screw is a screw whose head is substantially flush with, or lower than, the upper edge of the through hole unit.

If a ring stopper is used as the slip-off prevention member, a ring groove formed in the inner wall of the through hole unit along its inner circumference is used as the slip-off prevention member engaging unit. This groove is sufficient if it has a structure allowing the stopper ring used as the slip-off prevention member to engage from the outside in the radial direction of the stopper ring.

If a caulking projection is used as the slip-off prevention member, as the slip-off prevention member engaging unit, a ring groove is formed in the inner wall of the through hole unit along its inner circumference or a recess into which the caulking projection is inserted is formed in the inner wall of the through hole unit. These groove and recess are sufficient if they have a structure allowing the caulking projection caulked and used as the slip-off prevention member to engage from the outside, and are formed near at the central area, rather than the lower end, of the through hole unit while taking the removal of the caulking projection thereafter into consideration.

Although the medical substituting element for hard tissues of this invention has the through hole unit, screw stopper, and slip-off prevention member engaging unit, one or a plurality of stems may be formed on the lower surface (the surface in contact with the hard tissues) of the medical substituting element for hard tissues, if necessary for each application, aiming at convenience of position alignment when the medical substituting element for hard tissues is mounted on the hard tissues, or for other objects. In order to mount the medical substituting element for hard tissues with means other than the fixation screws, a central stem, a condylar stem, a fin, a screw, a keel, a hook, a flange formed to cover the anterior or posterior side of hard tissues (bone), a porous, rough surface, a indented rough surface, a beam, or the like may be formed if necessary.

If the subject medical substituting element for hard tissues is a constituent (fixed to hard tissues) of an artificial joint of a hinge type or a hemi-hinge type, a hinge axis, a hinge bearing, or the like may be formed if necessary on the upper surface (the surface opposite to the surface in contact with the hard tissues) of the medical substituting element for hard tissues.

In mounting the medical substituting element for hard tissues of this invention on the hard tissues, the fixation screw is inserted into the through hole unit of the medical substituting element for hard tissues, the fixation screw is threaded into the hard tissues until the head of the fixation screw is stopped by the screw stopper or until a desired amount of gap between the head of the fixation screw and the screw stopper is retained, and thereafter the slip-off prevention member is engaged with the above-described slip-off prevention member engaging unit.

Engagement of the slip-off prevention member with the slip-off prevention member engaging unit is performed, if the slip-off prevention member is a slip-off prevention screw, by meshing the slip-off prevention screw with the female thread as the slip-off prevention member engaging unit. If the slip-off prevention member is a stopper ring, it is performed by engaging the stopper ring with the groove as the slip-off prevention member engaging unit. If the slip-off prevention member is a caulking projection formed on the head of the fixation screw, it is performed by threading the slip-off screw into hard tissues to a predetermined depth, and thereafter, bending outward (this work is called "caulking") the caulking projection formed on the head of the fixation screw to enter the end of the caulking projection into the groove or recess as the slip-off prevention member engaging unit.

By engaging the slip-off prevention member with the slip-off prevention member engaging unit in the above manner, it is possible to prevent the spontaneous rotation and slip-off of the fixation screw threaded into the hard tissues. Accordingly, loosening of the medical substituting element for hard tissues is hard to occur, which might otherwise be caused by the spontaneous rotation and slip-off of the fixation screw after the mount on the hard tissues.

The slip-off prevention member once engaged with the slip-off prevention member engaging unit can be removed, for example, if the slip-off prevention member is a slip-off prevention screw, by rotating the slip-off prevention screw in a predetermined direction. If the slip-off prevention member is a stopper ring, it can be released by nipping the desired portion of the stopper ring with a pair of plier or the like with sharp tips and squeezing them in the direction of reducing its diameter to dismount it from the slip-off prevention member engaging unit. If the slip-off prevention member is a caulking projection, it can be performed by threading the fixation screw further deep into the hard tissues and making it again upright. After the slip-off prevention member is removed, the fixation screw can be removed easily by rotating it in the direction opposite to that of threading it into the hard tissues.

Next, the artificial joint of this invention is to be described.

As described previously, the artificial joint of this invention comprises a first constituent member mounted on an osteotomized surface of the one bone constituting a joint and a second constituent member mounted on an osteotomized surface of the other bone constituting the joint, the first and second constituent members abutting against each other directly or via a slide member, or being coupled together by a member with an open/close mechanism. The artificial joint of this invention has the features that the first or second constituent member comprises: one or a plurality of through hole units into which fixation screws are inserted; a screw stopper for stopping the fixation screw inserted into the through hole unit at the position where the head of the fixation screw becomes lower than the upper end of the through hole unit; and a slip-off prevention member engaging unit formed in the inner wall of the through hole unit at the position higher than the screw stopper, wherein after the fixation screw inserted into the through hole unit is threaded into hard tissues, a slip-off prevention member engages with the slip-prevention member engaging unit to ensure a slip-off prevention of the fixation screw.

Specifically, in the artificial joint of this invention, at least one of constituent members constituting the artificial joint is mounted on hard tissues with fixation screws, and the above-described slip-off prevention member engaging unit is formed at a predetermined position of the through hole unit of the constituent element into which the fixation screw is inserted. The other constituent elements and materials of this constituent member may be similar to a conventional artificial joint.

The invention relating to an artificial joint is applicable to various types of artificial joints of the type capable of fixation at least one of the constituent members on hard tissues with fixation screws. Examples of such artificial joints to be enumerated are an artificial knee joint (unicompartmental replacement type, total replacement type, non-constraint type, hemi-constraint type, constraint type, hinge type, hemi-hinge or rotation-hinge type), meniscus bearing type, tibia plateau type, and the like), an artificial hip joint, an artificial joint with an artificial bone, an artificial shoulder joint, an artificial ankle joint, an artificial elbow joint, and the like.

In the artificial joint of this invention, in mounting a constituent member made of the medical substituting element for hard tissues of this invention on the hard tissues, the fixation screw is inserted into the through hole unit formed on the constituent member, the fixation screw is threaded into the hard tissues, and thereafter, the slip-off prevention member is engaged with the slip-off prevention member engaging unit. It is, therefore, possible to prevent the spontaneous rotation and slip-off of the fixation screw once threaded. Accordingly, loosening of the artificial joint is hard to occur, which might otherwise be caused by the spontaneous rotation and slip-off of the fixation screw after the mount on the hard tissues.

Further, even if a polyethylene slide member (e.g., tibial bearing insert) is disposed on the constituent member (e.g., tibial tray) fixed to hard tissues with fixation screws, the slide member is hard to be broken (penetrated and crashed) which might otherwise be caused by the spontaneous rotation and slip-off of the fixation screw.

Furthermore, for a constituent member of the type which is fixed by striking a fixation stem or the like into hard tissues, it is often difficult to elongate the stem or the like because a work space for its insertion is limited. However, if the fixation screw is used, this screw can be easily elongated, and with the longer fixation screw, the fixation strength can be easily increased. Accordingly, with the artificial joint of this invention, it is easy to mount the constituent member made of the medical substituting element for hard tissues of this invention, with better fixation effects, and the surgery is easier than an artificial joint of the type having no constituent member mounted on a bone with fixation screws. Still further, less invasion alleviates a physical load on a patient and therefore the recovery after surgery is better.

In the artificial joint of this invention, the constituent elements other than the constituent member made of the medical substituting element for hard tissues of this invention can be mounted in the manner similar to a conventional manner.

The medical substituting element for hard tissues of this invention has the slip-off prevention member engaging unit in the inner wall of the through hole unit of the medical substituting element for hard tissues at its predetermined position. Therefore, the fixation screw is inserted into the through hole unit and threaded into the hard tissues until the head of the fixation screw is stopped by the screw stopper or until a desired amount of gap between the head of the fixation screw and the screw stopper is retained, and thereafter the slip-off prevention member is engaged with the above-described slip-off prevention member engaging unit. It is therefor possible to prevent the spontaneous rotation and slip-off of the fixation screw once threaded.

If as the slip-off prevention member a slip-off prevention screw having the threading rotation direction opposite to the fixation screw is used and the female thread portion meshing with the slip-off prevention screw is used as the slip-off prevention member engaging unit, and if the slip-off prevention screw is meshed with the female thread portion, then even if the fixation screw once threaded into the hard tissues intends to spontaneously rotate and move back outside, a slip-off of the fixation screw is impossible because the rotation direction is that of threading the slip-off prevention screw into the hard tissues. Further since vibrations of the hard tissues cannot transmit directly to the slip-off prevention screw, it is hard for the slip-off prevention screw to spontaneously rotate and move back outside.

If the ring stopper is used as the slip-off prevention member and the ring groove is formed in the inner wall of the through hole unit along the inner circumference thereof as the slip-off prevention member engaging unit to allow it to engage with the ring stopper from the outside in the radial direction of thereof, then even if the fixation screw once threaded into the hard tissues intends to spontaneously rotate and move back outside, this motion is prevented by the ring stopper so that the fixation screw is impossible to move back outside.

If the caulking projection formed on the head of the fixation screw is used as the slip-off prevention member and the recess or ring groove is formed in the inner wall of the through hole unit to allow the end of the caulking projection caulked to engage from the outside, then even if the fixation screw once threaded into the hard tissues intends to spontaneously rotate and move back outside, this motion is prevented by the caulking projection caulked so that the fixation screw is impossible to move back outside.

As described above, the medical substituting element for hard tissues of this invention can prevent the fixation screw from moving back outside after the mount on the hard tissues. Therefore, loosening of the medical substituting element for hard tissues is hard to occur, which might otherwise be caused by the spontaneous rotation and slip-off of the fixation screw after the mount on the hard tissues.

Embodiments of the invention will be described with reference to the accompanying drawings.

Figure 1A:
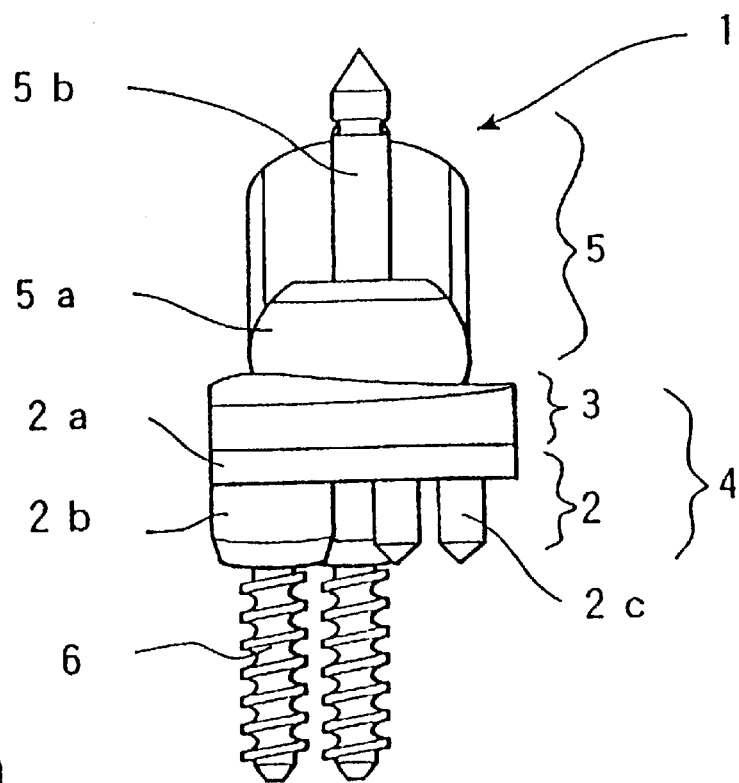
FIG. 1(a) is a front view showing an example of an artificial knee joint of a unicompartmental replacement type included in artificial joints of the invention.
Figure 1B:
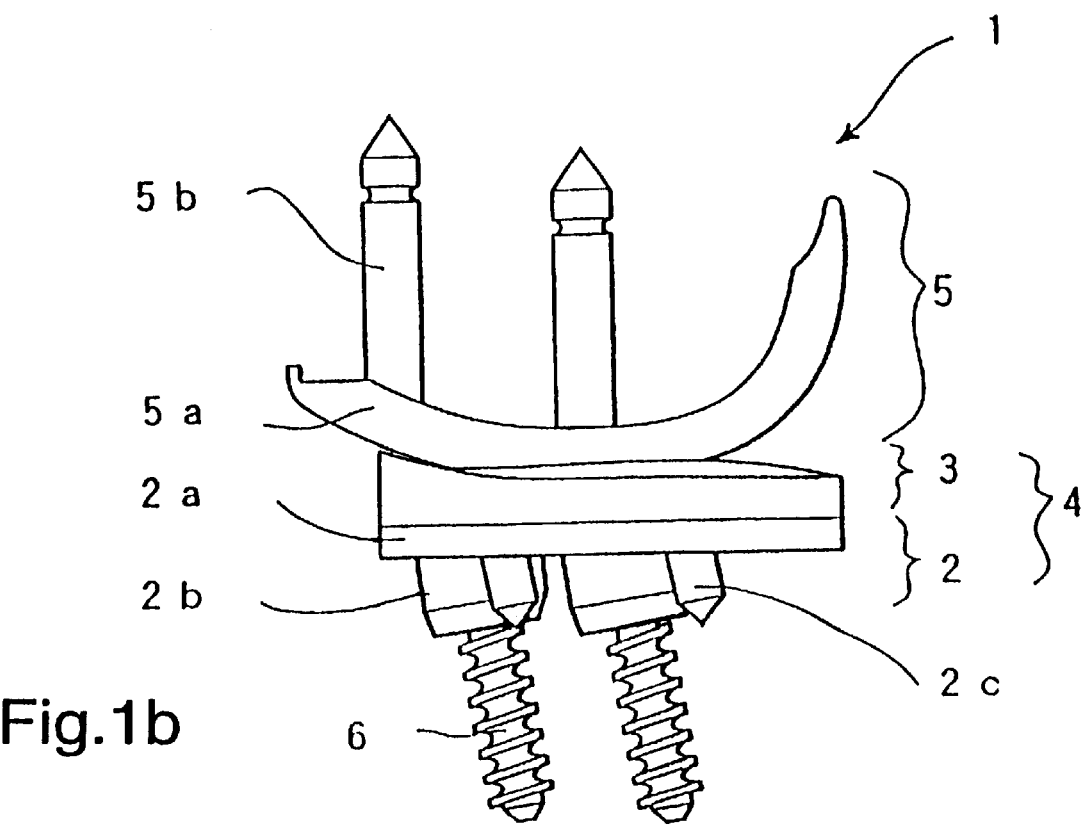
FIG. 1(b) is a side view of the artificial knee joint of the unicompartmental replacement type shown in FIG. 1(a).

FIG. 1(a) is a front view showing an example of an artificial knee joint 1 when in use of a knee of unicompartnmental replacement type included in artificial joints of the invention, and FIG. 1(b) is a side view of the artificial knee joint 1 when in use of the knee of unicompartmental replacement type shown in FIG. 1(a).

The artificial knee joint 1 (for right leg) shown in FIGS. 1(a) and 1(b) has a tibial component 4 and a femoral component 5, the tibial component 4 being constituted by a tibial tray 2 and a tibial bearing insert 3 detachably mounted on the upper surface (the surface on the side of the femur when in use) of the tibial tray 2.

The tibial tray 2 has a plate unit 2a made of titanium, and two projections or sleeves 2b and two stems 2c formed on the bottom surface (the surface in contact with the tibia when in use) of the plate unit 2a. The bottom surface of the plate unit 2a is rough and porous. The projections 2b and stems 2c are formed to obliquely direct toward the back side of the tibia so that they reach the tibial cortex when the tibial tray 2 is mounted on the tibia. Each projection 2b has a through hole unit (not shown in FIG. 1) passing through the projection 2b in the longitudinal direction thereof. A fixation screw 6 is inserted into this through hole unit. An engaging unit (not shown) is formed on the upper surface of the plate unit 2a, for detachably mounting the tibial bearing insert 3 on the upper surface of the plate unit 2a. The details of this through hole unit will be later described.

The tibial bearing insert 3 is made of ultra-macromolecular polyethylene, its bottom surface (the surface in contact with the tibial tray 2 when in use) is formed with an engaging unit (not shown) for engagement with the upper surface of the tibial tray 2, and its top surface (the surface in contact with the femoral component 5 when in use) has a predetermined curved surface. This tibial bearing insert 3 is mounted on the top surface of the tibial tray 2 when in use and functions as a slide member for the femoral component 5. Since the tibial bearing insert 3 is detachably mounted on the tibial tray 2, if it is abraded after operation, only this tibial bearing insert 3 can be replaced.

The femoral component 5 has a plate unit 5a made of cobalt-chrome alloy and curved in a predetermined shape and two stems 5b formed on the upper surface of this plate unit 5a. The upper surface (the surface in contact with the femur when in use) of the plate unit 5a is an indented rough surface.

In the artificial knee joint 1 of the invention of a knee of unicompartmental replacement type comprising the tibial component with the tibial tray and tibial bearing insert 3 and the femoral component 5, the tibial tray 2 corresponds to the medical substituting element for hard tissues of this invention.

Figure 2:
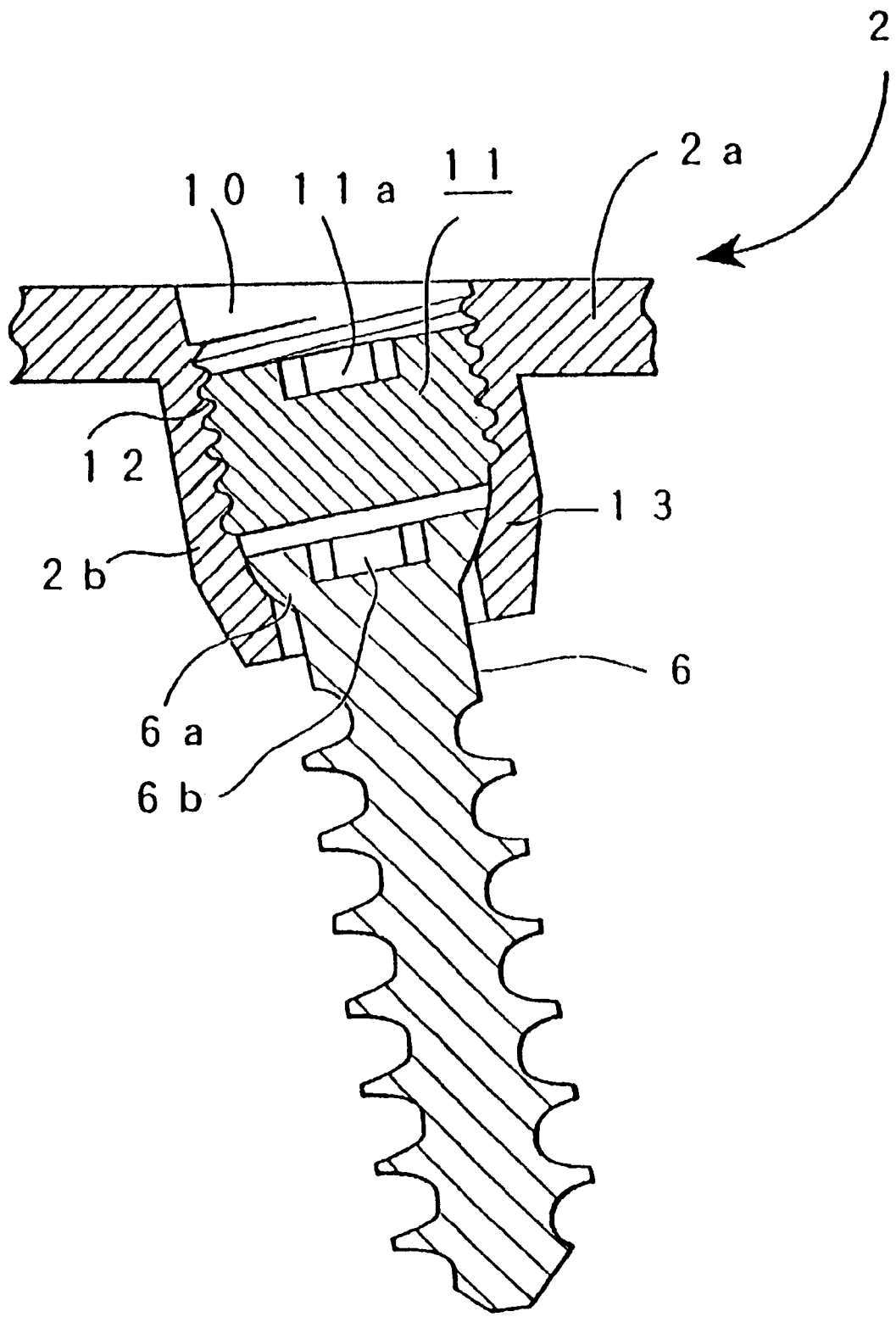
FIG. 2 is a cross sectional view showing an example of a tibial tray of a unicompartmental type artificial knee joint made of a medical substituting element for hard tissues of this invention, in which a slip-off prevention engaging unit of the tibial tray is shown in an enlarged view.

Specifically, as shown in FIG. 2, each of the two projections 2b formed on the bottom surface of the plate unit 2a constituting the tibial tray 2 is formed with a through hole unit 10 passing through the projection 2a in the longitudinal direction. As a slip-out prevention member engagement unit, a female thread portion 12 meshing with a left-handed slip-out prevention screw is formed in the inner wall of each through hole unit 10. Near at the lower end portion (the end on the insertion side into the tibia) of the through hole unit 10, a screw stopper 13 is formed for stopping the right-handed fixation screw 6 at the position where the head 6a of the fixation screw 6 is lower than the upper end of the through hole unit 10, when the fixation screw 6 is inserted into the through hole unit 10. The female thread portion 12 is formed in the inner wall of the through hole at the position higher than the screw stopper 13.

Figure 3A:
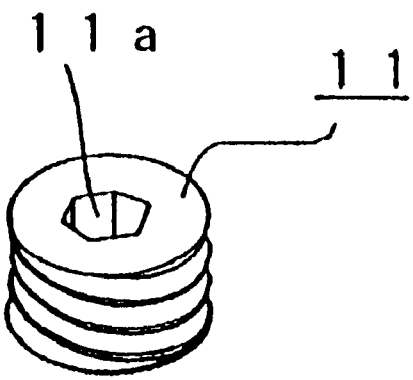
FIG. 3(a) is a perspective view of a slip-off prevention screw uses as the slip-off prevention member of the tibial tray shown in FIG. 2.

The slip-out prevention screw 11 is a left-handed screw as described above. Although this slip-out prevention screw 11 has no head as shown in FIG. 3(a), a hexagonal hole 11a is formed in the upper surface of the slip-out prevention screw 11 in order to allow a rod spanner of a hexagonal cross section to enter this hole 11a and rotate the slip-out prevention screw 11.

Figure 3B:
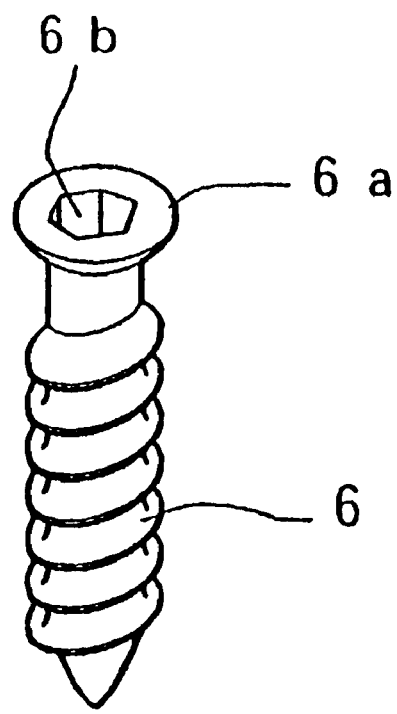
FIG. 3(b) is a perspective view of a fixation screw of the tibial tray shown in FIG. 2.

The fixation screw 6 is a right-handed screw as described above, and has a flat head as shown in FIG. 3(b). A hexagonal hole 6b is formed in the head 6a of the fixation screw 6 in order to allow a rod spanner of a hexagonal cross section to enter this hole 6b and rotate the fixation screw 6.

Figure 4:
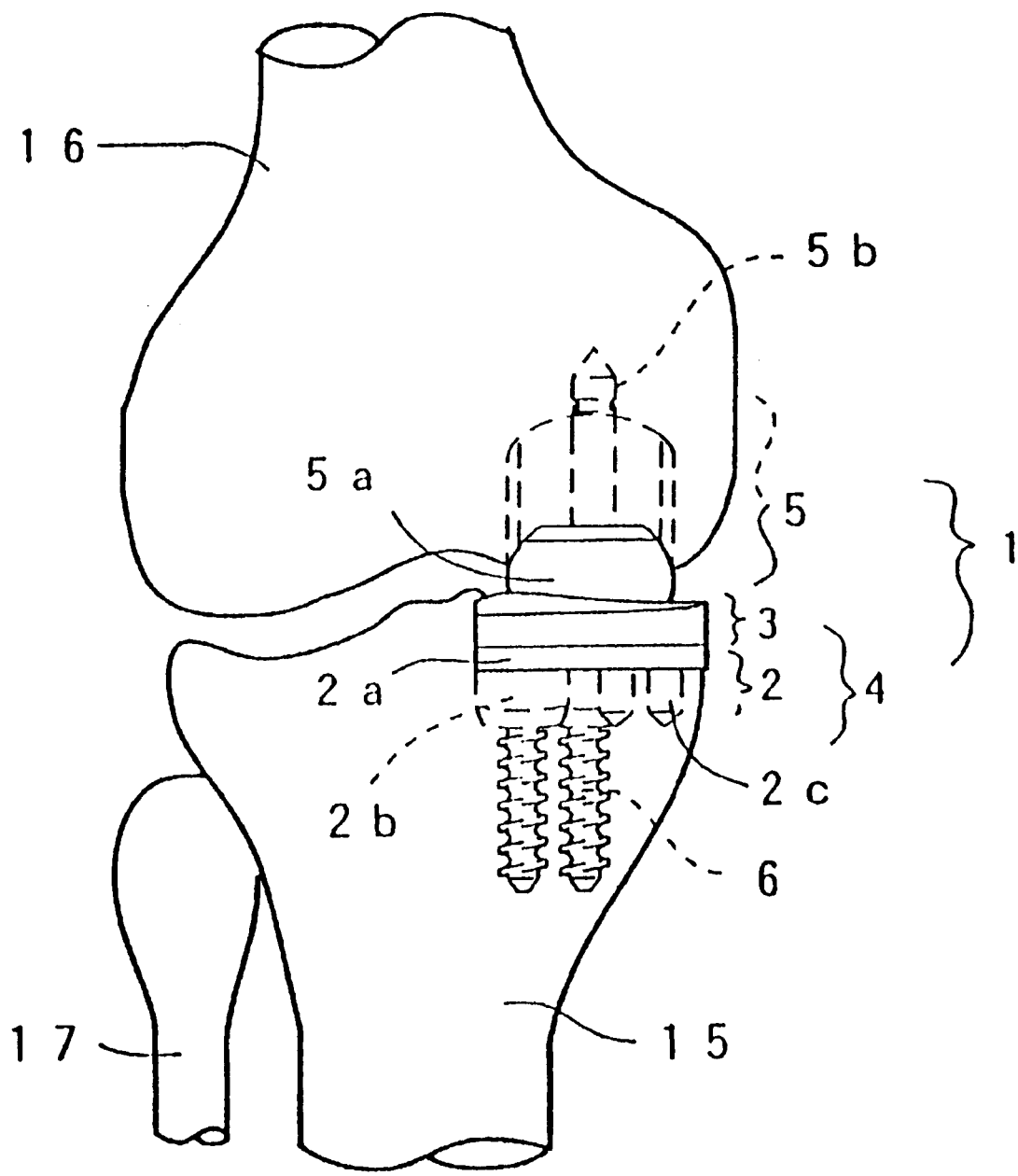
FIG. 4 is a front view illustrating a use state of the artificial knee joint of the unicompartmental replacement type shown in FIG. 1.

As described earlier, the artificial knee joint 1 is an unicompartmental replacement type artificial knee joint, and as shown in FIG. 4 substitutes part of the function of the knee joint. In mounting the artificial knee joint 1 on a knee, the tibial tray 2 is mounted on the proximal end of a tibia 15 at a predetermined position, and the femoral component 5 is mounted on the distal end of the femur 16 at a predetermined position. The tibial bearing insert 3 is mounted on the upper surface of the tibial tray 2.

The tibial tray 2 is mounted on the tibia 15, for example, in the following manner. First, a predetermined area of the proximal end of the tibia 15 is ground to form a flat surface, holes for inserting the projections 2b and stems 2c of the tibial tray 2 thereinto are formed in the flat surface area and thereafter, the projections 2b and stems 2c are inserted into these holes to align the position of the tibial tray 2. Next, each fixation screw 6 is inserted into the through hole unit 6 and threaded into the tibia 15, until the head 6a of the fixation screw 6 abuts against the screw stopper 13 or until a desired amount of gap is formed between the head 6a of the fixation screw 6 and the screw stopper 13, to thereby fix the tibial tray 2 to the tibia 15. Thereafter, the slip-out prevention screw 11 is threaded into and meshed with the female thread portion 12 to ensure a slip-out prevention of the fixation screw 6. A combination of the fixation screw 6, slip-out prevention screw 11, female thread portion 12, and screw stopper 13 is preferably arranged so as to leave a desired amount of gap between the lower surface of the slip-out prevention screw 11 and the top surface of the fixation screw 6.

With the slip-out prevention screw 11 being meshed with the female thread portion 12, even if the fixation screw 6 once threaded into the hard tissues (tibia) is spontaneously rotated and moved back outside, this motion is stopped because the rotation direction is the direction of threading the slip-out prevention screw 11 into the through hole unit 10. Accordingly, after the tibial tray 2 is mounted on the tibia 15, loosening of the tibial tray 2 is not likely to be formed by the spontaneous rotation and back motion to outside of the fixation screw 6. For the position alignment of the tibial tray 2, bone cement may be used if necessary.

On the other hand, in mounting the femoral component 5 on the femur 16, for example, after a guide hole into which the stem 34b of the femoral component 5 is struck is formed in the distal end of the femur 16 at a predetermined position, the distal end of the femur 41 is ground at a predetermined area and thereafter, the stem 5b is struck into the femur 16 along the guide hole. In mounting the femoral component 5, bone cement may be used if necessary. Reference numeral 17 shown in FIG. 4 represents a fibula.

The tibial tray 2 constituting the artificial knee joint 1 uses the slip-out prevention screw 11 as a slip-out prevention member and uses the female thread portion 12 meshing with the slip-out prevention screw 11 as a slip-out prevention member engaging unit. As the slip-out prevention member, a stopper ring an example of which is shown in FIG. 5 may be used in addition to the slip-out prevention screw 11.

Figure 5:
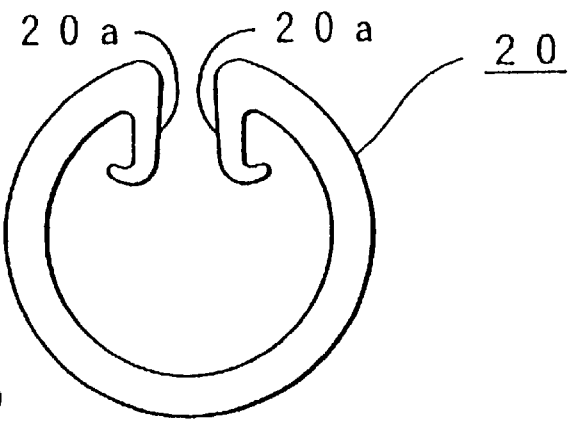
FIG. 5 is a plane view showing an example of a stopper ring as one of slip-off prevention members to be mounted on a medical substituting element for hard tissues of this invention.

The stopper ring shown in FIG. 5 has a holding unit 20a at each end of a cut-portion of a C-shaped concentric stopper ring. These holding units 20a are formed by bending both the ends of the cut-portion in generally an L-character shape and extending them inside of the C-shaped concentric stopper ring. The holding units 20a can be nipped by a pair of pliers or the like having narrow tips from the outside. Therefore, the diameter of the stopper ring 20 can be made smaller easily.

Figure 6:
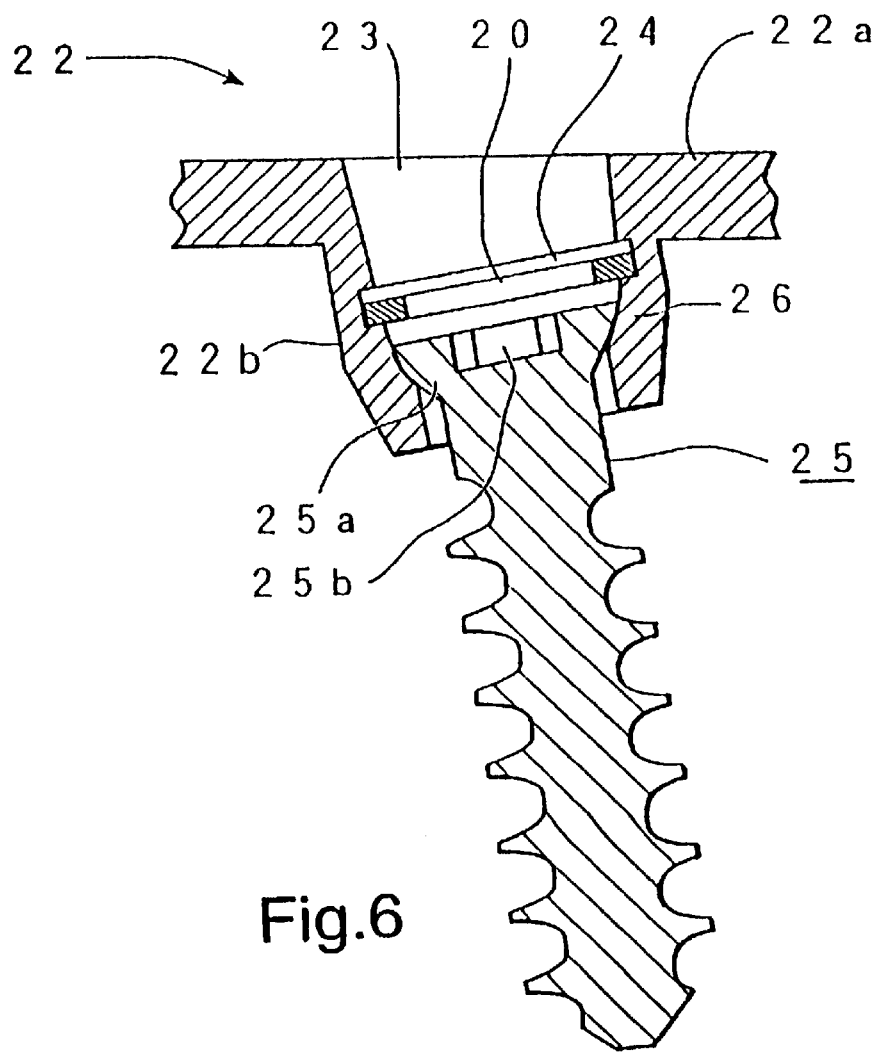
FIG. 6 is a cross sectional view showing another example of a tibial tray of a unicompartmental type artificial knee joint made of a medical substituting element for hard tissues of this invention, in which a slip-off prevention engaging unit of the tibial tray is shown in an enlarged view.

FIG. 6 shows an example of a tibial tray using this stopper ring 20 as the slip-out prevention member.

The tibial tray 22 shown in FIG. 6 has the same outer appearance as the tibial tray 2 shown in FIG. 2 except that the length of a projection 22b formed on the lower surface of a plate unit 22a constituting the tibial tray 22 is shorter than that shown in FIG. 2. Each projection 22b of the tibial tray 22 has a through hole unit 23 passing through the projection 22b in the longitudinal direction thereof. A ring groove 24 is formed in the circumferential inner wall of the through hole unit 23 at a predetermined position, the outside in the radial direction of the stopper ring 20 being engageable with the ring groove 24. This groove 24 corresponds to the slip-out prevention member engaging unit.

Near at the lower end portion (the end on the insertion side into the tibia) of the through hole unit 23, a screw stopper 26 is formed for stopping a fixation screw 25 at the position where the head 25a of the fixation screw 25 is lower than the upper end of the through hole unit 23, when the fixation screw 25 is inserted into the through hole unit 23. The groove 24 is formed in the inner wall of the through hole unit at the position higher than the screw stopper 26.

The tibial tray 22 shown in FIG. 6 is mounted, for example, in the following manner. First, similar to the tibial trader 2 shown in FIG. 1, a predetermined area of the proximal end of the tibia is ground to form a flat surface, a predetermined number of holes for inserting the projections 22b and stems (not shown) of the tibial tray 22 thereinto are formed in the flat surface area and thereafter, the projections 2b and stems 2c are inserted into these holes to align the position of the tibial tray 22. Next, each fixation screw 25 is inserted into the through hole unit 23 formed in the projection 22b and threaded into the tibia, until the head 25a of the fixation screw 25 abuts against the screw stopper 26 or until a desired amount of gap is formed between the head 25a of the fixation screw 25 and the screw stopper 26, to thereby fix the tibial tray 22 to the tibia 15. Thereafter, the two holding units 20a formed on the stopper ring 20 are nipped and squeezed with a pair of pliers or the like having sharp tips to reduce the diameter of the stopper ring 20. In this state, the stopper ring 20 is inserted into the through hole unit 23 and fitted into the groove 24. With the stopper ring 20 being fitted into the groove 24, a slip-out prevention of the fixation screw 25 is ensured. A combination of the stopper ring 20, groove 24, and fixation screw 25 is preferably arranged so as to leave a desired amount of gap between the bottom surface of the stopper ring 20 and the top surface of the fixation screw 25.

With the stopper ring 20 being fitted in the groove 24, even if the fixation screw 25 once threaded into the hard tissues (tibia) is spontaneously rotated and moved back outside, this motion is stopped by the stopper ring 20 and the fixation screw 25 cannot be moved back outside. Accordingly, after the tibial tray 22 is mounted on the tibia, loosening of the tibial tray 22 is not likely to be formed by the spontaneous rotation and back motion to outside of the fixation screw 25. The stopper ring 20 fitted in the groove 24 can be easily removed by nipping and squeezing the two holding units 20a from the outside with a pair of pliers or the like having sharp tips to reduce the diameter of the stopper ring 20. Reference numeral 25b shown in FIG. 6 represents a hexagonal hole in order to allow a rod spanner Of a hexagonal cross section to enter this hole and rotate the fixation screw 25.

Figure 7:
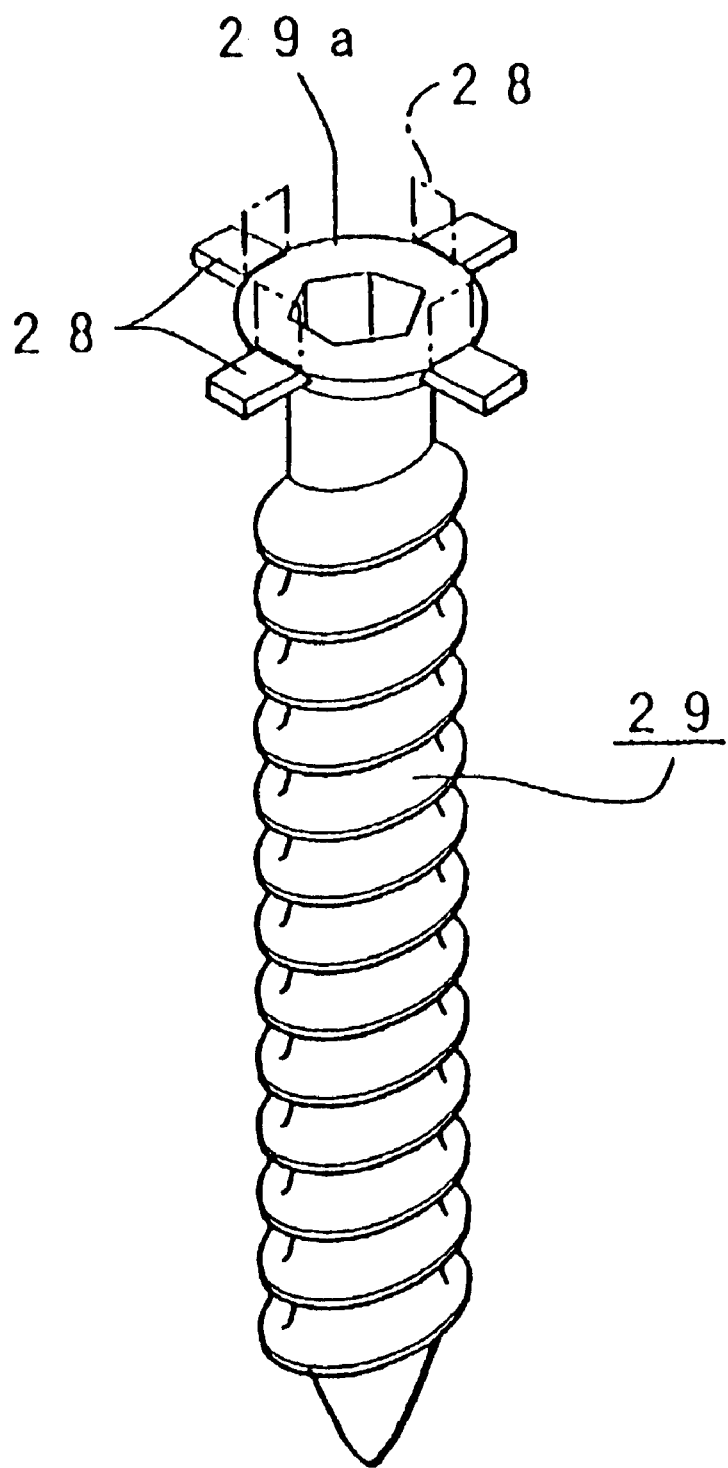
FIG. 7 is an oblique view showing an example of a caulking projection as one of slip-off prevention members to be mounted on a medical substituting element for hard tissues of this invention.

As the slip-out prevention member, caulking projections 28 examples of which are shown in FIG. 7 may also be used. These caulking projections 28 are formed upright on the head 29a of a fixation screw 29 as indicated by phantom lines (one-dot chain lines) in FIG. 7. As the slip-out prevention member engaging unit for these caulking projections 28, a ring groove or a recess formed in the inner wall of the through hole unit may be used. After the slip-out prevention screw 29 is threaded into hard tissues to a predetermined depth, these caulking projections 28 are caulked (bent outward) as indicated by solid lines in FIG. 7 to insert the end portions of the caulked projections into the slip-out prevention member engaging unit (groove or recess).

With the end portions of the caulked projections 28 being inserted into the slip-out prevention member engaging unit (groove or recess), even if the fixation screw 29 once threaded into the hard tissues (tibia) is spontaneously rotated and moved back outside, this motion is stopped by the caulked projections 28 and the fixation screw 29 cannot be moved back outside. Although four caulking projections 28 are shown in FIG. 7, the number of caulking projections 28 is not limited to four, but the number may be selected as desired in a range from four to six caulking projections.

As described so far in connection with the embodiments of the invention, the medical substituting element for hard tissues of this invention is not limited only to the tibial tray of an artificial knee joint of an unicompartmental replacement type. As described earlier, the invention relating to a medical substituting element for hard tissues is applicable to various types of medical substituting elements for hard tissues capable of being fixed to hard tissues with fixation screws, including a fixation metal jig (bone fixation plate) for surgical treatment of a fracture, a augmentation material (a device with a boss) for an artificial ligament or an artificial tendon, an artificial bone of the type which is attached to the bone with fixation screws, a tibial tray, a tibial component and a femoral component of an artificial knee joint, an acetabular component of an artificial hip joint, a tibial component and a talar component of an artificial ankle joint, aglenoidal component of an artificial shoulder joint, a humeral component and a ulnar component of an artificial elbow joint, an artificial bone head, and the like. The overall shape of the medical substituting element for hard tissues can be selected as desired depending upon each application.

The artificial joint of this invention may be such an artificial joint having partially at its constituent the medical substituting element for hard tissues of this invention, and is not limited only to the artificial knee joint of the unicompartmental replacement type. The invention relating to the artificial joint is applicable to various types of artificial joints having a constituent capable of being fixed to hard tissues with fixation screws, including an artificial knee joint (unicompartmental replacement type, total replacement type, non-constraint type, hemi-constraint type, constraint type, hinge type, hemi-hinge or rotation-hinge type), meniscus bearing type, tibial plateau type, and the like), an artificial hip joint, an artificial shoulder joint, an artificial ankle joint, an artificial elbow joint, an artificial joint with an artificial bone, and the like. The overall shape thereof can be selected as desired depending upon each application.

What is claimed is:

1. A medical substituting element for hard body tissues comprising:
   a member made of a medically inorganic solid material having one or a plurality of through hole units into which fixation screws are inserted, each of the one or plurality of through hole units including an integral sleeve protecting from said member;
   a fixation screw for each of said one or plurality of through hole units;
   a screw stopper surface formed in said sleeve for stopping said fixation screw inserted into said through hole unit at a position where a head of said fixation screw lies below an upper end of said sleeve;
   a slip-off prevention member,
   a slip-off preventing member engaging means for engaging said slip-off prevention member, said means formed in an inner wall of said sleeve at a position higher than said screw stopper surface;
   wherein in use, and after said fixation screw is inserted into said sleeve and is threaded into hard body tissues, said slip-off prevention member is engaged with said slip-off prevention member engaging means to ensure slip-off prevention of said fixation screw.

2. A medical substituting element for hard body tissues according to claim 1, and wherein said fixation screw passes through said sleeve along a longitudinal direction of said sleeve.

3. A medical substituting element for hard body tissues according to claim 1, wherein said slip-off prevention member engaging means comprises a ring groove formed in an inner circumferential surface of said sleeve, and said slip-off prevention member comprises a stopper ring.

4. A medical substituting element for hard body tissues according to claim 1, wherein said slip-off prevention member engaging means comprises a ring groove or recess formed in an inner circumferential surface of the sleeve, and said slip-off prevention member comprises a caulking projection formed on the head of said fixation screw.

5. A medical substituting element for hard body tissues according to claim 1, further comprising one or a plurality of stems formed on a side of said member adapted to abut against the hard body tissues.

6. A medical substituting element for hard body tissues according to claim 1, wherein said member comprises a tibial tray or a tibial component of an artificial knee joint.

7. A medical substituting element for hard body tissues according to claim 1, wherein said sleeve reaches the cortex of the tibia when in use.

8. A medical substituting element for hard body tissues according to claim 1, wherein said member comprises a bone fixation plate, a reinforcing member for an artificial ligament or an artificial tendon, an artificial bone of the type which is attached to a bone with fixation screws, a femoral component of an artificial knee joint, an acetabular component of an artificial hip joint, a tibial component or a tatar component of an artificial ankle joint, an acetabular tegmen side component of an artificial shoulder joint, a humeral component or a ulnar component of an artificial elbow joint, or an artificial bone head.

9. An artificial joint having a first constituent member mounted on a ground surface formed on one bone constituting a joint and a second constituent member mounted on a ground surface formed on the other bone constituting the joint, said first and second constituent members abutting against each other directly or via a slide member, or being coupled together by a member with an open/close mechanism, wherein said first or second constituent member comprises:
one or a plurality of through hole units into which one or a plurality of respective fixation screws are inserted;
a screw stopper for stopping said fixation screw inserted into said through hole unit, said screw stopper spaced vertically below an upper edge of said first or second constituent member but above an upper edge of said fixation screw;
a slip-off prevention member;
a slip-off prevention member engaging unit formed in an inner wall of said through hole unit for engagement by said slip-off prevention member,
wherein after said fixation screw is inserted into said through hole unit and threaded into hard body tissues, said slip-off prevention member is engaged with said slip-off prevention member engaging unit to ensure slip-off prevention of said fixation screw.

10. An artificial joint according to claim 9, wherein said first or second constituent member has a projection formed on its lower surface, and said through hole unit extends through said projection along a longitudinal direction of said through hole unit.

11. An artificial joint according to claim 9, further comprising one or a plurality of stems formed on a side of said artificial joint abutting against the hard body tissues.

12. An artificial joint according to claim 9 used for an artificial knee joint wherein said first constituent member is mounted on a ground surface formed on a shinbone and said second constituent member is mounted on a ground surface formed on a thighbone, and wherein said first constituent member comprises said one or a plurality of through hole units into which fixation screws are inserted.

13. An artificial joint according to claim 12, wherein said through hole unit extends through a projection formed on a lower surface of said first constituent member, said through hole unit extending through said projection along a longitudinal direction, and wherein said projection reaches the cortex of the tibia when in use.

14. An artificial joint according to claim 9, wherein the artificial joint is an artificial hip joint, an artificial joint with an artificial bone, an artificial shoulder joint, an artificial ankle joint, or an artificial elbow joint.

* * * * *